ated to a pH of between 2.8 and 6.5.

United States Patent [19]

Kandathil et al.

[11] Patent Number: 5,152,992
[45] Date of Patent: Oct. 6, 1992

[54] METHOD FOR CONTROL OF SOCIAL INSECTS WITH A HEMISALT OF A PERFLUOROALKANE SULFONIC ACID

[75] Inventors: Thomas V. Kandathil; Richard E. Keyel, Racine; James J. Leskowicz, Mt. Pleasant, all of Wis.

[73] Assignee: S. C. Johnson & Son, Inc., Racine, Wis.

[21] Appl. No.: 657,010

[22] Filed: Feb. 15, 1991

[51] Int. Cl.$^5$ .................... A01N 25/00; A01N 25/02; A01N 25/04
[52] U.S. Cl. .................................... 424/405; 424/84; 43/107; 43/111; 43/114; 43/131; 43/132.1
[58] Field of Search .................... 424/405, 84; 43/107, 43/111, 114, 132.1, 131

[56] References Cited

U.S. PATENT DOCUMENTS

| | | | |
|---|---|---|---|
| 4,092,110 | 5/1978 | Adolphi et al. | 427/440 |
| 4,540,711 | 9/1985 | Bettarini et al. | 514/720 |
| 4,582,901 | 4/1986 | Prestwich | 536/83 |
| 4,851,218 | 7/1989 | Hildebrandt et al. | 424/84 |
| 4,915,301 | 4/1990 | Munteanu | 239/45 |
| 4,921,696 | 5/1990 | Vander Meer et al. | 424/84 |
| 4,983,061 | 1/1991 | Demarest | 401/148 |

OTHER PUBLICATIONS

"Control of Wasps in Food Factories" Frank Jefkins, Food Trade Review, May 1961, p. 47.
Chapter 21, Fluorinated Sulfonamides, in *Synthesis and Chemistry of Agrochemicals*, Vander Meer et al.

*Primary Examiner*—Thurman K. Page
*Assistant Examiner*—Robert H. Harrison

[57] ABSTRACT

An aqueous formulation for the control of social insects, especially wasps, and a method for its use. The formulation contains insect attracting ingredients and a toxicant in water. The toxicant is a hemisalt preparation of a perfluoroalkane sulfonic acid which is partially neutralized to a pH of between 2.8 and 6.5.

5 Claims, No Drawings

METHOD FOR CONTROL OF SOCIAL INSECTS WITH A HEMISALT OF A PERFLUOROALKANE SULFONIC ACID

TECHNICAL FIELD

This invention relates to the field of insect control and particularly to a formulation of a concentration dependent insect toxicant that, when mixed with a suitable insect attracting ingredient, will be carried by the food gatherers of a group of social insects, such as a colony of wasps, whereupon such food is carried back to the wasps' home colony, thereby destroying it, as well as a method of use for this preparation.

BACKGROUND ART

There are two major passive methods for insect control: traps and toxic baits. Both types must incorporate some kind of insect attracting material in order to be effective. Food materials are often used as the insect attracting material. An example of a material attractive to wasps is U.S. Pat. No. 4,851,218 to Hildebrandt et al., "Method for Controlling Insects of the Family Vespidae Utilizing Interspecific Bait". Traps, whether of the sugar water in a bottle variety or the flypaper variety, are only effective on individual insects. Toxicant preparations can be formulated with different types of pesticides. Pesticides can be used in two major ways, for quick-kill or for so-called "delayed-kill."

Quick-kill pesticides which kill shortly after contact or ingestion, are desirable for control of populations of insects of non-aggregating behavior. Quick-kill pesticides are usually used as aerosol and spray insecticides which may be dispersed or formulated in aqueous, non-aqueous or partially aqueous systems for ease of dispensing.

Pesticides which have a "delayed kill action" are most useful for a different type of insect: the so-called social insect. "Delayed-kill" pesticides can derive their delayed kill action from intrinsic properties of the chemical, if the toxic moiety of the compound itself has a delayed release. Membrane barriers, microencapsulation, or even binding of the pesticide to a polymer substrate, have been used as methods for accomplishing this delayed release. "Delayed kill" pesticides can also be of the type that are not delayed release, but disrupt an insect's internal system. Disruption of certain internal systems will cause the insect to succumb after a period of days. A different type of "delayed kill" is obtained from a concentration dependent toxicant, which, at higher concentrations, would provide a quick-kill and at lower concentrations would not kill immediately. Such a toxicant, however, has a "delayed action kill" effect as the target insect is killed as a result of repeated consumption of the toxicant.

The social insects include such species as ants, termites, wasps and bees. (Wasps and bees include both social and non-social types.) Social insects by definition have a social hierarchy, with workers and foragers, males, and an egg-laying queen. Quick kill of individual forager insects does not affect the main colony. However, if a "delayed action" toxicant is mixed with an insect attracting ingredient, the foragers will carry the toxicant-attractant formulation back to the home colony where it is shared by larvae, workers, and queen. If sufficient toxicant is transported back into the nest, it is possible to eradicate the entire colony by trophallaxis (a mutual exchange of food) within a week or two, (if the toxicant is sufficiently effective in the amounts that reach the colony). In order to assure that sufficient toxicant is carried back to the nest, the toxicant-attractant formulation must not be repellent to the pest and must be protected from degradation.

Wasps, which include such insects as yellowjackets and hornets, as well as those commonly called wasps, were considered, in the Old Testament, to be a plague upon mankind. Not only do wasps sting, sometimes with fatal results, but they also cause damage to fruit crops and they kill honeybees. Probably the greatest problem presented to man by wasps, however, is their nuisance value. They often are present in large numbers around recreational sites or garbage dumps or similar sources of available food. Thus effective methods of control are desirable.

The use and importance of "delayed action" pesticides for the control of social insects is known in the art.

Historically it has been found that the most effective method of wasp control is the destruction of the home colony. However, the main drawback with this direct approach is the difficulty in locating the home colony.

Various species of wasps and hornets may have nests that are subterranean, within the structure of homes, or "aerial" (in trees, under roofs, etc.). A problem in eradicating the home colony for all three types is, as stated, locating the home colony. The second type especially presents an access problem: it is difficult to introduce an effective amount of a toxicant into a nest within an existing home since precautions to protect those living there are necessary.

U.S. Pat. No. 4,540,711 to Bettarini et al, "Method for Combatting Infestations of Insects and Acari and Compositions for Use in Said Method", discloses the use of a hydroaquinone diether in an insect attracting ingredient for control of ants, especially fire ants. The use of the compound for termite control is also suggested, since it is effective against termites and they are also social insects. The patent also points out that such poisoned insect attracting ingredient must still be appetizing to the ants, or it will not be eaten or carried back to the nest.

Another "delayed action" toxicant for termite control is disclosed in U.S. Pat. No. 4,582,901 to Prestwich, "Fluorinated Cellulose Esters and the Use Thereof as Termiticidal Compositions". This patent clearly states the need for "delayed action" toxicants for termite control:

> For a pesticide to be effective against termites and related pests it may have a somewhat delayed onset of activity. Termites typically feast upon a food supply and then return to their nest and regurgitate the food to be shared by those occupying the nest. Thus, a pesticide which instantly destroys the feeding termites has absolutely no effect upon those hatching on the nest. While the feeding termites are affected, those in the nest continue to multiply and thus the infestation remains.

The same considerations apply to any other type of social insect, and the Bettarini et al. patent similarly but not as completely discussed the "spreading action of delayed action toxicants".

The problems associated with the presence of wasps, especially around food processing and packaging plants, and the successful use of a delayed action chlorinated hydrocarbon insecticide for wasp colony destruction has been reported in Great Britain. ("Control of Wasps in Food Factories," Frank Jefkins, Food Trade Review, May 1961, p. 47). This solid insect attracting ingredient has been sold under the name Waspex. Wasp toxicant-attractant formulations can also be prepared and dispensed in the form of gels, syrups or liquids.

Since the insect attracting ingredient carrier for any "delayed action" toxicant formulation must be appetizing and non-repelling to the target insects, different insect attracting ingredients and different types of toxicant formulations must be used for different species.

Carbohydrate insect attracting ingredients are more generally acceptable than protein based insect attracting ingredients to wasps. Carbohydrates combined with small amounts of protein are also acceptable. Protein insect attracting ingredients are preferred by certain scavenging species. Protein insect attracting ingredients such as fish, chicken, etc., are highly susceptible to spoilage. Although antimicrobials and/or preservatives can prevent spoilage of protein insect attracting ingredients to some extent, these additives were found to be repellent to wasps. Many toxicants added to a insect attracting ingredient are unstable (decompose) in sunlight or air over a period of time making the toxicant-attractant formulation less effective. Toxicant decomposition products are often repellent to wasps and render the insect attracting ingredients unacceptable. Certain stabilizing agents such as antioxidants and surfactants can be used to stabilize the toxicants to some extent. However most of these additives tend to be repellent to wasps.

Aqueous insecticidal formulations are preferable to solid insecticidal formulations because a wasp must first cut a solid insect attracting ingredient into a piece of manageable size, then transport the piece back to the nest. The time and energy required to imbibe liquid toxicant-attractant formulation is less than is required to cut up the solid toxicant-attractant formulation. Thus, although transport times are the same, more toxicant is delivered to the nest per unit of time with liquids than with solids. Aqueous insecticidal formulations also have the advantage that they can satisfy the colony's need for water. For these reasons a stable water soluble toxicant is preferred.

Frequently used "delayed action" toxicants such as bendiocarb (2,2-dimethyl-1,3-benzodioxol-4-yl methyl carbamate) and Dursban (0,0-Diethyl-0-[3,5,6-trichloro-2-pyridyl]-phosphorothioate) are not water soluble and must be made water dispersible by the use of surfactants, organic solvents, and/or hydrotropes. The addition of such compounds to an aqueous insecticidal formulation, however, makes the formulation unattractive or even repellent to wasps. Another drawback of the dispersed or emulsified insecticide is that it can undergo phase separation in storage. The problem of such phase separation is that the insecticide will separate into the oil phase at the top, which will create inadequate and disproportionate delivery of toxicant-attractant formulation in the aqueous phase.

Although other "delayed action" toxicants such as Dipterex (dimethyl [2,2,2-trichloro-1-hydroxy ethyl]-phosphonate), acephate (O,S-dimethyl acetylphosphoramidothioate) and borax are water soluble, it was found that the toxicant-attractant formulation prepared using these were not very attractive to wasps.

A further consideration for an effective "delayed action" toxicant is a careful balancing of the concentration and the kill effect. Too great a concentration of the pesticide will repel wasps and will produce too quick a kill for effectiveness in eradication of the home colony. A smaller concentration of toxicant allows a wasp to make repeated visits to the source of the toxicant-attractant formulation. After each visit, the wasp returns home, carrying some of the toxicant with it. The cumulative effect of the toxicant destroys the home colony, an effect that does not occur if the initial kill is too quick.

The fluorinated sulfonamides have been found to be effective "delayed action" insecticides for such social arthropods as ants. This is discussed in Ch. 21, Fluorinated Sulfonamides, in *Synthesis and Chemistry of Agrochemicals*, Vander Meer et al., (American Chemical Society, Washington, D.C., 1987). However, since such compounds are of limited solubility in water, they cannot be used with aqueous insect attracting ingredient components.

The Vander Meer et al. chapter also stated that perfluorooctane sulfonic acid form and its potassium salt provided good delayed activity on ants. The use of various amides of perfluoro compounds for the control of arthropods is disclosed by U.S. Pat. No. 4,921,696 to Vander Meer et al.

U.S. Pat. No. 4,092,110 to Adolphi et al. discloses the use of compounds of the formula $C_nF_{2n+1}SO_3M$ where n is an integer from 1 to 14 and M is hydrogen or a cation for treatment of wood or wood based materials from "animal pests," especially termites.

SUMMARY DISCLOSURE OF THE INVENTION

The present invention is an aqueous concentration dependent toxicant formulation for the control of social flying insects, especially wasps, and a method for its use. The preparation includes both toxicant and insect attracting ingredient components.

It has been found that the perfluoroalkane sulfonic acid salts are generally insoluble in water and thus unsuitable for use with an aqueous insect attracting ingredient composition by itself. Perfluoroalkane sulfonic acid is water soluble, but such solutions have very low pH (a 1% solution of the acid in water has a pH of 1 or less), creating problems with the insect attracting ingredient and in handling the solution. A toxicant-attractant formulation produced using perfluoroalkane sulfonic acid has such a low pH that the preparation is not readily taken by wasps and appears to repel them. The acidic preparations are not preferred either for consumer or for pest control use due to the hazardous nature of highly acidic preparations.

A partially neutralized preparation of perfluoroalkane sulfonic acid, however, is not very acidic and has sufficient water solubility for such use and produces a toxicant-attractant formulation that is very attractive to wasps. Perfluoroalkane sulfonic acid can be partially neutralized to raise pH by incremental addition of a base to produce a sufficiently water soluble and attractive toxicant-attractant formulation. Sufficient water solubility and higher pH can be achieved by using a hemisalt preparation of perfluoroalkane sulfonic acid. It has been found that the hemisalt preparation of perfluoroalkane sulfonic acid is an effective concentration dependent toxicant The hemisalt preparation is also stable in carbohydrate solutions, the preferred insect attracting ingredient for such insects.

Solubility of the toxicant in water is one problem solved by the present invention; effective concentration limits for such a preparation is another. It was found that very low toxicant concentrations of the hemisalt of perfluoroalkane sulfonic acid (approximately 0.001%) were effective, although sufficient kill of a home colony for adequate population control was much slower than for higher concentrations. Concentrations of 1.0% proved to kill so effectively that the wasps did not live long enough to transport to and share sufficient toxicant with the home colony to destroy it.

BEST MODE FOR CARRYING OUT THE INVENTION

A preferred method of use of the toxicant-attractant formulation of the present has been found to be to place the formulation into a covered container. Liquid toxicant-attractant formulation can be dispensed through a wick extending into the liquid and protruding through and above the container cover. (Other dispensing means, such as a humming bird feeder-type station with permeable membrane, absorbent pads, or any seepage device may also be used.) To be effective, the container should be placed in an area frequented by the wasps, preferably above ground level to prevent access by children or animals.

SELECTION OF FORMULATIONS TO BE FIELD TESTED

Preparations were first tested in the laboratory to screen out those formulations that did not have the desired combination of attractancy (or non-repellency) and "delayed kill" effect.

Mortality of toxicants/additives, etc. of wasps and repellency were studied under controlled conditions in the laboratory. Laboratory tests were conducted with standard insecticides such as bendiocarb, Dursban, Dipterex, acephate, and borax (described before). It was found that all were ineffective as concentration dependent toxicants for wasps. Then various toxicant-attractant formulations with perfluoroalkane sulfonic acids and perfluoroalkane sulfonic acid salts were tested. It was found, as discussed before, that both concentration levels and pH were important variables. Wasps were trapped and brought to the lab. Ten worker wasps were placed in a 1 cubic foot wire mesh cage and given access to a 10% sucrose solution and acclimated overnight. The next day the sugar solution was removed and was replaced by two solutions, one with a particular level of toxicant in the insect attracting ingredient and the other one without toxicant (insect attracting ingredient solution alone). The number of dead wasps was recorded at various time intervals, up to 24 hours. Four replicate cages were used for each concentration of each toxicant. Generally, three concentrations of two toxicants were tested in each experiment. If mortality occurred at moderate concentrations of a particular toxicant, but not a higher concentrations it was concluded that the test toxicant was toxic to wasps. It was also assumed that the test toxicant was a repellent to wasps at higher concentrations.

Since wasps under laboratory or forced-feeding (no other food sources available) would consume toxicant-attractant formulations that they might normally avoid in the open, preliminary, non-controlled field tests were conducted to select formulations to be thoroughly tested for colony and nest destruction under extensive and controlled conditions in three regions.

Next, fields with wasp problem/population were identified and insect attracting ingredient stations were established there. Containers with the insect attracting ingredient alone (no toxicant) and with formulations containing the insect attracting ingredient and different levels of concentrations of toxicant were placed on bait stations close to each other. The number of wasps feeding from each container was counted at various time intervals. Materials which had shown little repellency in the laboratory often showed repellency in the field. This phenomenon is probably due to the fact that, as said earlier, wasps in the open field (in their natural habitat) had free choice of food sources, while wasps in the cages had no such choice. Toxicant-attractant formulations frequently visited and fed by wasps in the field were considered non-repellent and those which were not visited and fed by wasps were considered repellent.

PREPARATION OF AQUEOUS HEMISALT

Perfluoroalkane sulfonic acids were prepared by ion exchange from commercially purchased potassium perfluoroalkane sulfonates. A representative batch of these potassium perfluoroalkane sulfonates was tested and found to contain perfluoroalkane chain lengths ranging from $C_4F_9$ to $C_8F_{17}$. A hemisalt of perfluoroalkane sulfonic acids can be made by mixing an aqueous solution of a base with an aqueous solution of the acid to prepare an aqueous formulation having a pH between 2.8 and 6.5, preferably pH 4.0 to 6.5, most preferably pH 5.0 to 6.0, and optimally approximately pH 5.5. The base can have any suitable base, such as metal hydroxides of sodium, potassium, lithium, calcium, magnesium, zinc, aluminum or zirconium; ammonium hydroxide; primary, secondary or tertiary amines; primary, secondary or tertiary alkanolamines; or tetra alkylammonium hydroxides (alkyl being methyl, ethyl, propyl, or butyl).

PREPARATION OF AQUEOUS FORMULATIONS

An insect attracting ingredient preparation of carbohydrates in water, preferably containing a mixture of corn syrup, sucrose, maltodextrine, a protein, and optionally a preservative, was made up. The optimal preparation contained 10% to 20% corn syrup, 5% to 15% sucrose, 0.5% to 5% maltodextrine, 1% to 10% commercially available proteins, and 0.001% to 0.20% of Kathon (preservative), the balance being water. To this was added the hemisalt preparation of perfluoroalkane sulfonic acid, preferably 0.001% to 1.5% of the total weight, and most preferably 0.02% to 0.03%.

Gel formulations were also prepared by addition of a suitable gelling agent to the preparation.

Suitable gelling agents would include such things as cellulose fibers, polysaccharides, or clays (natural or synthetic). Such an agent would be preferably present in from 0.5% to 10% by weight of the total weight of the formulation.

A preparation of the formulation in a gel form provides several advantages. It provides necessary water for the foragers and the colony, it minimizes water loss through evaporation (which would happen in open field on a sunny day) and it provides packaging flexibilities for the finished product.

FIELD TEST EXPERIMENTAL METHODOLOGY

For wasp population abundance studies, three bait stations were placed out at each of several sites, preferably near known wasp nests. Each station was kept filled with the aqueous insect attracting ingredient with no toxicant added. Each day, the number of insects feeding at the insect attracting ingredient station was counted and recorded. This indicated when populations were abundant enough for testing. It also gave baseline abundance for toxicity tests. Such testing was carried out at least a week in advance of toxicant testing.

This allowed yellowjacket foragers to be trained to the stations. (Similar results to those reported below were obtained without such training, but initial wasp visitations were lower). Individual wasps were netted and then marked with a small drop of paint. Wasps readily returned to the station after marking. All wasps visiting the same station were marked with the same color. Each station had a different color. The number of marked and unmarked wasps feeding at each station was recorded. Also, the number of marked and unmarked wasps leaving the nest cavity in 5 minutes was recorded. This constituted the precount.

After precounts were established, actual toxicant testing was begun. The formulation with the insect attracting ingredient alone was, at some sites, then replaced with a formulation containing toxicant as well as the insect attracting ingredient. Other sites continued to have only the formulation without the toxicant to serve as controls. Periodically afterwards, the number of marked and unmarked wasps feeding at the stations and the number exiting the nests were recorded. A decline indicated mortality. At longer intervals, nests were excavated to determine the number of workers alive in the nest, status of the brood with the nest, and whether the queen was alive.

The presence of marked wasps leaving the nest indicated that at least some wasps from that nest had been feeding on a station containing toxicant and insect attracting ingredient. Movement of wasps between stations was also tracked with the marked wasps.

Testing was carried out at sites in Hawaii, Wisconsin and Georgia. At each test site, three different concentrations of toxicant were tested and population densities both at the insect attracting ingredient stations and at the home nests were monitored over time. The wasps present at each location were species of yellowjackets. The toxicant-attractant formulations field tested were all previously screened, as discussed above, and it was found that they were well taken by wasps under choice-feeding conditions.

Approximately 100 different formulations were tested, using slightly different proportions of insect attracting ingredients, preservatives, bases, and many different levels of toxicant. All formulations were within the parameters discussed above. Four of the formulations tested are given below:

| | 1 | 2 | 3 | 4 |
|---|---|---|---|---|
| Tap Water | 73.96185 | 73.9614 | 70.9535 | 70.9615 |
| Animal protein Hydrolyzed (Polypro 5000) | — | — | 3.0000 | — |
| Wheat Protein Hydrolyzed (Hydrotriticum) | — | — | — | 3.0000 |
| Maltodextrin (Star Dry 10) | 3.00000 | 3.0000 | 3.0000 | 3.0000 |
| Sucrose (C & H Sugar) | 8.00000 | 8.0000 | 8.0000 | 8.0000 |
| Corn Syrup (Cornsweet 95) | 15.00000 | 15.0000 | 15.0000 | 15.0000 |
| Kathon LX | 0.00800 | 0.0080 | 0.0160 | 0.0080 |

-continued

| | 1 | 2 | 3 | 4 |
|---|---|---|---|---|
| (Preservative) Perfluoroalkane sulfonic acid | 0.02990 | 0.0279 | 0.0293 | 0.0293 |
| Sodium Hydroxide | 0.00025 | — | 0.0012 | 0.0012 |
| Tetramethyl ammonium hydroxide | — | 0.0027 | — | — |
| Total | 100.00000 | 100.0000 | 100.0000 | 100.0000 |

The acid, bases and Kathon were used from dilute water solutions and water corrections adjusted accordingly.

Over 300 individual observations were made at the sites. Three concentrations of toxicant (0.03%, 0.014% and 0.007%) were tested at each station to allow for field observation of wasp feeding preferences. All concentrations proved effective. The results of the observations for each toxicant concentration were averaged.

In Lake Herrick, Ga., the wasp species tested was *Vespula maculifrons*. Locations for the stations were selected near known nests. Zero hours marks the beginning of the test, when the toxicant-attractant formulation solution was placed in the station. Negative time counts are precounts. The results of these tests for the stations are:

| | Average Number of Wasps Per Station | | |
|---|---|---|---|
| | % Concentration of Toxicant | | |
| Time (hrs) | 0.03 (6 stations) | 0.014 (9 stations) | 0.007 (9 stations) |
| −3.6 | 44.0 | 31.7 | 38.1 |
| 1.2 | 38.9 | 45.2 | 64.0 |
| 2.4 | 25.0 | 36.2 | 61.2 |
| 20.6 | 1.8 | 2.7 | 2.4 |
| 24.2 | 1.6 | 0.7 | 1.4 |

As the numbers show, the stations with the lower toxicant concentrations showed an increase in wasp concentration over the precount figure. It is assumed that this increase reflects the fact that additional wasps located and visited the station after the precount. Wasps partaking of the lower toxicant concentration formulations were able to revisit the stations before their deaths. Wasps having visited the station with higher toxicant concentrations began to die off sooner than those who visited and fed on the lower toxicant level compositions. Thus, stations with higher toxicant levels showed no visitation increase after precount.

As discussed before, wasps visiting a station were marked. No wasps marked at one station were ever found at another station. At 20.6 hours and 24.2 hours, no marked wasps were found at any station, at any concentration, indicating that, by that time, all wasps that had visited a station had died.

The number of wasps leaving a nest was also monitored. Five nests were observed, the five nests containing wasps that were marked as having visited three different stations. Nest activity showed a decline comparable to that observed on the stations.

| Time (hrs) | # Exits per 5 min. (averaged) |
|---|---|
| −2.8 | 83.500 |
| 1.7 | 117.500 |

-continued

| Time (hrs) | # Exits per 5 min. (averaged) |
|---|---|
| 3.0 | 91.000 |
| 20.0 | 14.125 |
| 21.3 | 19.375 |
| 24.8 | 17.125 |

After 20.0 hours, no marked wasps were observed exiting the nests. Excavation of two nests after the 24.8 hour count showed that worker populations had been reduced, but some workers and the queen were still alive. Presumably, the nest excavations were performed before the toxicant had spread to the queen and remaining workers. Excavation of the remaining nests after five days showed that none of the workers nor the queen were alive.

In order to test the effectiveness of the toxicant-attractant formulation in areas without nearby nests, stations, one for each toxicant concentration, were set up at three locations, chosen at random, away from identified nests. Similar wasp populations visiting the stations were noted.

| Time (hrs) | Average Number of Wasps per Station % Concentration of Toxicant | | |
|---|---|---|---|
| | 0.03 | 0.014 | 0.007 |
| −0.2 | 22.3 | 31.3 | 22.0 |
| 1.0 | 15.3 | 22.3 | 35.0 |
| 2.7 | 15.3 | 22.3 | 29.0 |
| 3.9 | 3.0 | 14.0 | 16.3 |
| 4.8 | 2.3 | 10.7 | 8.7 |
| 5.8 | 3.3 | 6.0 | 7.0 |
| 7.2 | 6.3 | 3.0 | 4.0 |
| 23.3 | 0.0 | 1.0 | 5.3 |
| 24.3 | 1.0 | 1.7 | 3.7 |
| 25.1 | 2.3 | 1.7 | 6.3 |
| 27.1 | 1.0 | 1.3 | 6.0 |

The numbers showed a similar pattern of decline, both in numbers of marked and unmarked wasps, as in the other tests.

To study the effect of toxicant concentration on bait palatability, three stations (each with one toxicant concentration) were set up at four sites and monitored. Three stations with no toxicant present but only the insect attracting ingredient were set up at two sites to serve as a check on the effects of external factors such as weather or natural population decline. The data showed that the decline in the number of wasps was attributable to the presence of the toxicant, for no decline (only a variation) showed for the stations without toxicant.

Since wasps returning to a particular colony could have fed from stations with any of these toxicant concentrations, results were pooled for final reporting in the table that follows.

| Time (hrs) | Average Number of Wasps Per Station With Toxicant (Average of all concentrations) | No Toxicant |
|---|---|---|
| −26.4 | 20.8 | 5.3 |
| 48.0 | 1.6 | 11.2 |
| 100.6 | 0.0 | 4.5 |
| 115.6 | 0.0 | 7.3 |
| 141.7 | 0.1 | 14.8 |
| 165.9 | 0.8 | 36.2 |

Excavation of nine nests in the vicinity of the toxicant-containing stations, performed at eleven days, found all wasps within the nest dead.

It should be understood that this figure does not mean that any nest would be destroyed in less than two weeks. Total kill time will vary, depending upon the size and population of a home nest and the amount of toxicant being carried back to that nest.

The amount of toxicant being carried back to a nest, as discussed, depends not only on the number of wasps visiting the site and then returning to the nest, but also on the concentration of the toxicant in the station.

Similar studies were carried out in Racine, Wisconsin, with *Vespula germanica* and in Hilo, Hi., with *Vespula pensylvanica*.

The results were similar, with the exception of the fact that to destroy entire extensive colonies (colonies of very high population such as tens of thousands) requires a large quantity of toxicant-attractant formulation and several days.

OTHER INSECTS

Similar studies were conducted in Racine, Wis., on honeybees (*Apis mellifera*), with almost identical results. All bees within a hive were found to be dead within 24 hours after access to the aqueous insecticidal formulation of the present invention. Studies were conducted on honeybees, not because honeybees are considered a nuisance insect, but to ascertain if the formulation would be effective against a non-desirable bee species, the so-called Africanized honeybee or killer bee. Field tests with such bees were not feasible to conduct, due to the ferocity of the bees and the possibility of lethal venom dosages to field personnel.

INDUSTRIAL APPLICABILITY

Toxicant-attractant formulation preparations according to the present invention can be used to control populations of wasps (including hornets and yellowjackets) wherever such insects create a problem. Picnic and park areas frequently have yellowjacket problems, as do any areas where garbage is stored. Food processing or production areas also have wasp problems. The formulation appears also useful for eradication of killer bee colonies.

What we claim is:

1. A method for controlling populations of social insects comprising placing, in an area accessible to and frequented by such social insects, a container of an aqueous insecticidal formulation comprising a hemisalt preparation of a sulfonic acid of the formula $C_XF_{2X+1}SO_3H$, where X is 4–8, the acid being partially neutralized with a base to a pH of between 2.8 and 6.5, wherein the hemisalt preparation comprises between 0.001% and 1.0% by weight of the formulation, wherein the base used to neutralize the sulfonic acid is selected from the group consisting of hydroxides of sodium, potassium, lithium, calcium, magnesium, zinc, aluminum or zirconium; ammonium hydroxide; primary, secondary or tertiary amines; primary, secondary or tertiary alkanolamines; or tetra alkylammonium hydroxides, the formulation further comprising an insect attracting ingredient mixture of between 10% and 20% corn syrup, between 5% and 15% sucrose, between 0.5% and 5% maltodextrine, between 1% and 10% of a protein, and between 0.001% and 0.2% of a preservative, the balance being water, and allowing the social insects to feed therefrom, thus providing the social insects with a concentration dependent toxicant which the social insects will then carry back to their home colony, thus effecting the kill of both the social insects initially feeding upon the formulation and of those who feed upon the formulation carried by those social insects back to the home colony.

2. A method for controlling populations of social insects comprising placing, in an area accessible to and frequented by such social insects, a container of an aqueous insecticidal formulation comprising a hemisalt preparation, wherein the hemisalt preparation comprises between 0.001% and 1.0% by weight of the formulation, of a sulfonic acid of the formula $C_XF_{2X+1}SO_3H$, where X is 4-8, the acid being partially neutralized with a base to a pH of between 2.8 and 6.5, the formulation further comprising an insect attracting ingredient mixture of between 10% and 20% corn syrup, between 5% and 15% sucrose, between 0.5% and 5% maltodextrine, between 1% and 10% of a protein, and between 0.001% and 0.2% of a preservative, the balance of the formulation being water, and allowing the social insects to feed therefrom, thus providing the social insects with a concentration dependent toxicant which the social insects will then carry back to their home colony, thus effecting the kill of both the social insects initially feeding upon the formulation and of those who feed upon the formulation carried by those social insects back to the home colony.

3. A method according to claim 2 wherein the base used to neutralize the sulfonic acid is selected from the group consisting of hydroxides of sodium, potassium, lithium, calcium, magnesium, zinc, aluminum or zirconium; ammonium hydroxide; primary, secondary and tertiary amines; primary, secondary and tertiary alkanolamines; or tetra alkylammonium hydroxides.

4. A method according to claim 2 wherein the aqueous insecticidal formulation further comprises between 0.5% and 10% of a gelling agent.

5. A method according to claim 2 wherein the container comprises a reservoir with a wicking mechanism protruding therefrom.

* * * * *